US006964979B2

(12) United States Patent
Gopalsamy et al.

(10) Patent No.: US 6,964,979 B2
(45) Date of Patent: Nov. 15, 2005

(54) R-ENANTIOMERS OF PYRANOINDOLE DERIVATIVES AND THE USE THEREOF FOR THE TREATMENT OF HEPATITIS C VIRUS INFECTION OR DISEASE

(75) Inventors: Ariamala Gopalsamy, Mahwah, NJ (US); John W. Ellingboe, Ridgewood, NJ (US); Tarek S. Mansour, New City, NY (US)

(73) Assignee: Wyeth, Madison, NJ (US)

( * ) Notice: Subject to any disclaimer, the term of this patent is extended or adjusted under 35 U.S.C. 154(b) by 45 days.

(21) Appl. No.: 10/441,983

(22) Filed: May 20, 2003

(65) Prior Publication Data

US 2004/0029947 A1 Feb. 12, 2004

Related U.S. Application Data

(60) Provisional application No. 60/382,148, filed on May 21, 2002.

(51) Int. Cl.[7] .................. A61K 31/407; C07D 491/052
(52) U.S. Cl. ....................................... 514/411; 548/432
(58) Field of Search .......................... 548/432; 514/411

(56) References Cited

U.S. PATENT DOCUMENTS

| | | | |
|---|---|---|---|
| 3,843,681 A | 10/1974 | Demerson et al. | 260/326.14 R |
| 3,880,853 A | 4/1975 | Demerson et al. | 260/247.5 FP |
| 3,939,178 A | 2/1976 | Demerson et al. | 260/326.28 |
| 3,974,179 A | 8/1976 | Demerson et al. | 260/326.28 |
| 4,012,417 A | 3/1977 | Demerson et al. | 260/326.5 SA |
| 4,036,842 A | 7/1977 | Dobson et al. | 260/293.58 |
| 4,070,371 A | 1/1978 | Demerson et al. | 260/326.29 |
| 4,076,831 A | 2/1978 | Demerson et al. | 424/274 |
| 4,118,394 A | 10/1978 | Demerson et al. | 260/326.28 |
| 4,179,503 A | 12/1979 | Asselin et al. | 424/248.51 |
| 4,501,899 A | 2/1985 | Abraham et al. | 548/432 |
| 4,515,961 A | 5/1985 | Demerson et al. | 548/432 |
| 4,520,203 A | 5/1985 | Abraham et al. | 548/432 |
| 4,544,757 A | 10/1985 | Demerson et al. | 548/432 |
| 4,585,877 A | 4/1986 | Demerson et al. | 548/432 |
| 4,604,469 A | 8/1986 | Demerson et al. | 548/432 |
| 4,670,462 A | 6/1987 | Katz et al. | 514/411 |
| 4,686,213 A | 8/1987 | Ferdinandi et al. | 514/161 |
| 4,785,015 A | 11/1988 | McKittrick et al. | 514/411 |
| 4,810,699 A | 3/1989 | Sabatucci et al. | 514/161 |
| 4,822,781 A | 4/1989 | Katz et al. | 514/161 |
| 4,822,893 A | 4/1989 | Failli | 548/432 |
| 4,960,902 A | 10/1990 | Failli | 548/432 |
| 5,071,853 A | 12/1991 | Bigge et al. | 514/290 |
| 5,128,363 A | 7/1992 | Failli | 514/411 |
| 5,223,517 A | 6/1993 | Müller | 514/339 |
| 5,578,734 A | 11/1996 | Vecchi | 548/432 |
| 5,599,946 A | 2/1997 | Vincenzo et al. | 548/432 |
| 5,633,388 A | 5/1997 | Diana et al. | 548/305.7 |
| 5,776,967 A | 7/1998 | Kreft et al. | 514/411 |
| 5,824,699 A | 10/1998 | Kreft et al. | 514/411 |
| 5,830,905 A | 11/1998 | Diana et al. | 514/322 |
| 5,830,911 A | 11/1998 | Failli et al. | 514/411 |
| 6,066,741 A | 5/2000 | Vigano et al. | 548/432 |
| 6,110,955 A | 8/2000 | Nudelman et al. | 514/411 |
| 6,177,440 B1 | 1/2001 | Bach et al. | 514/292 |
| 6,297,260 B1 | 10/2001 | Bandarage et al. | 514/327 |
| 6,331,638 B1 | 12/2001 | Raghavan et al. | 548/432 |
| 6,365,605 B1 | 4/2002 | Lavielle et al. | 514/338 |
| 6,383,768 B1 | 5/2002 | De Francesco et al. | 435/15 |
| 6,410,583 B1 | 6/2002 | Labelle et al. | 514/411 |

FOREIGN PATENT DOCUMENTS

| | | | |
|---|---|---|---|
| WO | WO 93/17680 | 9/1993 | |
| WO | WO 98/40066 | 9/1998 | ......... A61K/31/225 |
| WO | WO 98/40078 | 9/1998 | ......... A61K/31/62 |
| WO | WO 01/28555 | 4/2001 | ......... A61K/31/355 |
| WO | WO 02/00167 | 1/2002 | |
| WO | WO 02/04425 | 1/2002 | ......... C07D/235/00 |
| WO | WO 02/46170 | 6/2002 | ......... C07D/239/00 |
| WO | WO 02/46171 | 6/2002 | ......... C07D/239/42 |

OTHER PUBLICATIONS

Humber et al., "*Etodolac (1,8–Diethyl01,3,4,9–tetrahydropyrano[3,4–b]indole–1–acetic Acid) : A Potent Antiinflammatory Drug. Conformation and Absolute Configuration of Its Active Enantiomer*", J. Med. Chem., 29, 871–874 (1986).
Hepatology, 1997, vol. 26 (Supp. 1), pp. 2S–10S.
Purcell, *Hepatology*, 1997, vol. 26 (Supp. 1), pp. 11S–14S.
Bartenschlager, *Antiviral Chemistry and Chemotherapy*, vol. 8 (4), 1997, pp. 281–301.
Bartenschlager et al.,*J. General Virology*, 2000, vol. 81, part 7, pp. 1631–1648.
Ferrari et al., *J. Virology*, 1999, vol. 73 (2), pp. 1649–1654.
Takamizawa et al., *J. Virology*, 1991, vol. 65 (3), pp. 1105–1113.
Courtin, *Helv. Chim. Acta*, 1983, vol. 66 (1), pp. 68–75.
McKittrick et al., *J. Heterocyclic Chem.*, 1990, vol. 27 (7), pp. 2151–2163.

Primary Examiner—Taofiq Solola
(74) Attorney, Agent, or Firm—Fitzpatrick, Cella, Harper & Scinto

(57) ABSTRACT

The invention is directed to a compound and a pharmaceutical composition of the formula:

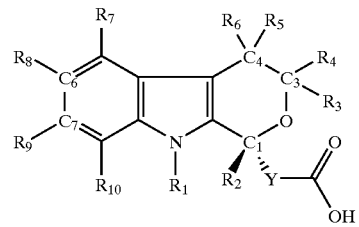

Wherein substitutions at $R_1$, $R_2$, $R_3$–$R_{12}$, and Y are set forth in the specification.

14 Claims, No Drawings

R-ENANTIOMERS OF PYRANOINDOLE DERIVATIVES AND THE USE THEREOF FOR THE TREATMENT OF HEPATITIS C VIRUS INFECTION OR DISEASE

This application claims the benefit of U.S. Provisional Patent Application Ser. No. 60/382,148, filed May 21, 2002. That application is hereby incorporated by reference herein in its entirety.

BACKGROUND OF THE INVENTION

1. Field of the Invention

This invention is directed to pharmaceutical compositions containing stereoisomers of pyranoindole derivatives and processes for their preparation.

2. Related Background Art

Hepatitis C is a common viral infection that can lead to chronic Hepatitis, cirrhosis, liver failure, and hepatocellular carcinoma. Infection with the Hepatitis C virus (HCV) leads to chronic Hepatitis in at least 85% of cases, is the leading reason for liver transplantation, and is responsible for at least 10,000 deaths annually in the United States (Hepatology, 1997, 26 (Suppl. 1), 2S–10S).

The Hepatitis C virus is a member of the Flaviviridae family, and the genome of HCV is a single-stranded linear RNA of positive sense (Hepatology, 1997, 26 (Suppl. 1), 11S–14S). HCV displays extensive genetic heterogeneity; at least 6 genotypes and more than 50 subtypes have been identified.

There is no effective vaccine to prevent HCV infection. The only therapy currently available is treatment with interferon-α (INF-α) or combination therapy of INF-α with the nucleoside analog ribavirin (Antiviral Chemistry and Chemotherapy, 1997, 8, 281–301). However, only about 40% of treated patients develop a sustained response, so there is a need for more effective anti-HCV therapeutic agents.

The HCV genome contains a number of non-structural proteins: NS2, NS3, NS4A, NS4B, NS5A, and NS5B (J. General Virology, 2000, 81, 1631–1648). NS5B is a RNA-dependent RNA polymerase which is essential for viral replication, and therefore, the inhibition of NS5B is a suitable target for the development of therapeutic agents.

In the following U.S. patents, pyranoindole derivatives are disclosed and the compounds are stated to have antidepressant and antiulcer activity: U.S. Pat. No. 3,880,853 (Apr. 29, 1975), U.S. Pat. No. 4,118,394 (Oct. 3, 1978). In U.S. Pat. No. 4,179,503 (Dec. 18, 1979) pyranoindoles are disclosed and stated to have diuretic activity. In the following U.S. patents, pyranoindole derivatives are disclosed and the compounds are stated to have antiinflammatory, analgesic, antibacterial, and antifungal activity: U.S. Pat. No. 3,843,681 (Dec. 22, 1974), U.S. Pat. No. 3,939,178 (Feb. 17, 1976), U.S. Pat. No. 3,974,179 (Aug. 10, 1976), U.S. Pat. No. U.S. Pat. No. 4,070,371 (Jan. 24, 1978), U.S. Pat. No. 4,076,831 (Feb 28, 1978). In the following U.S. patents, pyranoindole derivatives are disclosed and the compounds are stated to have antiinflammatory and analgesic activity: U.S. Pat. No. 4,670,462 (Jun. 2, 1987), 4,686,213 (Aug. 11, 1987), U.S. Pat. No. 4,785,015 (Nov 15, 1988), U.S. Pat. No. 4,810,699 (Mar. 7, 1989), 4,822,781 (Apr. 18, 1989), U.S. Pat. No. 4,960,902 (Oct. 2, 1990). In U.S. Pat. No. 5,776,967 (Jul. 7, 1998), and U.S. Pat. No. 5,830,911 (Nov. 3, 1998), pyranoindole derivatives are disclosed and compounds are said to inhibit cyclooxegenase-2 and be useful for treating arthritic disorders, colorectal cancer, and Alzheimer's disease.

Also, in the following U.S. patents, processes for preparing pyranoindole derivatives are disclosed: U.S. Pat. No. 4,012,417 (Mar. 15 1977), U.S. Pat. No. 4,036,842 (Jul. 19, 1977), 4,585,877 (Apr. 29, 1986), U.S. Pat. No. 4,822,893 (Apr. 18, 1989). Processes for the resolution of racemic pyranoindole derivatives are disclosed in the following U.S. Pat. No. : 4,501,899 (Feb. 26, 1985), U.S. Pat. No. 4,515,961 (May 7, 1985), U.S. Pat. No. 4,520,203 (May 28, 1985), U.S. Pat. No. 4,544,757 (Oct. 1, 1985).

U.S. provisional patent application No. 60/382,148, filed May 21, 2002, and which is hereby incorporated by reference in its entirety, provides other examples of compounds.

BRIEF SUMMARY OF THE INVENTION

This invention relates to a pharmaceutical composition comprising stereoisomers of pyranoindole derivatives, processes for their preparation, and pharmaceutical compositions containing them and to their use in the treatment of Hepatitis C viral infection.

In accordance with this invention there is provided a pharmaceutical composition comprising a compound represented by formula (A):

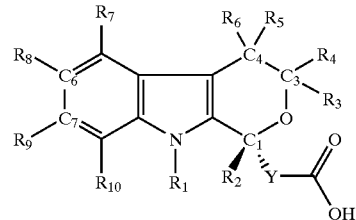

wherein:

$R_1$ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;

$R_2$ is H, a straight chain alkyl of 1 to 12 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, an alkoxyalkyl of 2 to 12 carbon atoms, an arylalkyl or alkylaryl of 7 to 12 carbon atoms, a cyanoalkyl of 1 to 8 carbon atoms, an alkylthioalkyl of 2 to 16 carbon atoms, a cycloalkyl-alkyl of 4 to 24 carbon atoms, a substituted or unsubstituted aryl, or a heteroaryl;

$R_3$–$R_6$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or $R_5$ and $R_6$ together with the ring carbon atom to which they are attached form a carbonyl group;

$R_7$–$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, alkylthio of 1 to 8 carbon atoms, trifluoromethoxy, trifluoroethoxy, trifluoromethylthio, trifluoroethylthio, acyl of 1 to 7 carbon atoms, COOH, COO-alkyl, CONR$_{11}$R$_{12}$, F, Cl, Br, I, CN, CF$_3$, NO$_2$, alkylsulfinyl of 1 to 8 carbon atoms, alkylsulfonyl of 1 to 6 carbon atoms, pyrrolidinyl, or thiazolidinyl;

R$_{11}$–R$_{12}$ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl;

Y is a bond, CH$_2$, CH$_2$CH$_2$, aryl, or R$_2$ and Y together with the ring carbon atom to which they are attached may additionally form a spirocyclic cycloalkyl ring of 3 to 8 carbon atoms; or a crystalline form or a pharmaceutically acceptable salt thereof; and a pharmaceutically acceptable carrier.

In one embodiment of the invention the pharmaceutical compositions comprise: (R)-5-cyano-8-methyl-1-propyl-1, 3,4,9-tetrahydropyrano[3,4-b]indol-1-yl]acetic acid; (R)-5-cyano-8-fluoro-1-propyl-1,3,4,9-tetrahydropyrano[3,4-b] indol-1-yl]acetic acid; (R)-5,8-dichloro-1-propyl-1,3,4,9-tetrahydropyrano[3,4-b]indol-1-yl]acetic acid; or (R)-5-cyano-6-fluoro-8-methyl-1-propyl-1,3,4,9-tetrahydropyrano[3,4-b]indol-1-yl]acetic acid.

For purposes of this invention the term "alkyl" includes both straight and branched alkyl moieties, preferably of 1 to 8 carbon atoms. The term "alkenyl" refers to a radical aliphatic hydrocarbon containing one double bond and includes both straight and branched alkenyl moieties of 2 to 7 carbon atoms. Such alkenyl moieties may exist in the E or Z configurations; the compounds of this invention include both configurations. The term "alkynyl" includes both straight chain and branched moieties containing 2 to 7 carbon atoms having at least one triple bond. The term "cycloalkyl" refers to alicyclic hydrocarbon groups having 3 to 12 carbon atoms and includes but is not limited to: cyclopropyl, cyclobutyl, cyclopentyl, cyclohexyl, cycloheptyl, norbornyl, or adamantyl. For purposes of this invention the term "aryl" is defined as an aromatic hydrocarbon moiety and may be substituted or unsubstituted. An aryl may be selected from but not limited to, the group: phenyl, α-naphthyl, β-naphthyl, biphenyl, anthryl, tetrahydronaphthyl, phenanthryl, fluorenyl, indanyl, biphenylenyl, acenaphthenyl, acenaphthylenyl, or phenanthrenyl groups. In one embodiment the substituted aryl may be optionally mono-, di-, tri- or tetra-substituted with substituents selected from, but not limited to, the group consisting of alkyl, acyl, alkoxycarbonyl, alkoxy, alkoxyalkyl, alkoxyalkoxy, cyano, halogen, hydroxy, nitro, trifluoromethyl, trifluoromethoxy, trifluoropropyl, amino, alkylamino, dialkylamino, dialkylaminoalkyl, hydroxyalkyl, alkoxyalkyl, alkylthio, —SO$_3$H, —SO$_2$NH$_2$, —SO$_2$NHalkyl, —SO$_2$N(alkyl)$_2$, —CO$_2$H, CO$_2$NH$_2$, CO$_2$NHalkyl, and —CO$_2$N(alkyl)$_2$. Preferred substituents for aryl and heteroaryl include: alkyl, halogen, amino, alkylamino, dialkylamino, trifluoromethyl, trifluoromethoxy, arylalkyl, and alkylaryl.

For purposes of this invention the term "heteroaryl" is defined as an aromatic heterocyclic ring system (monocyclic or bicyclic) where the heteroaryl moieties are five or six membered rings containing 1 to 4 heteroatoms selected from the group consisting of S, N, and O, and include but is not limited to: (1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, pyrrolidinyl; (2) a bicyclic aromatic heterocycle where a phenyl, pyridine, pyrimidine or pyridizine ring is: (i) fused to a 6-membered aromatic (unsaturated) heterocyclic ring having one nitrogen atom; (ii) fused to a 5 or 6-membered aromatic (unsaturated) heterocyclic ring having two nitrogen atoms; (iii) fused to a 5-membered aromatic (unsaturated) heterocyclic ring having one nitrogen atom together with either one oxygen or one sulfur atom; or (iv) fused to a 5-membered aromatic (unsaturated) heterocyclic ring having one heteroatom selected from O, N or S.

For the purposes of this invention the term "alkoxy" is defined as C1–C12alkyl-O—; the term "aryloxy" is defined as aryl-O—; the term "heteroaryloxy" is defined as heteroaryl-O—; wherein alkyl, aryl, and heteroaryl are as defined above.

For purposes of this invention the term "arylalkyl" is defined as aryl-C1–C6-alkyl-; arylalkyl moieties include benzyl, 1-phenylethyl, 2-phenylethyl, 3-phenylpropyl, 2-phenylpropyl and the like.

For purposes of this invention the term "alkylaryl" is defined as C1–C6-alkyl-aryl-.

For purposes of this invention the term "alkylthio" is defined as C1-C6-alkyl-S—.

For purposes of this invention "alkoxyalkyl," "cycloalkylalkyl," "alkylthioalkyl," "aryloxyalkyl," and "heteroaryloxyalkyl" denote an alkyl group as defined above that is further substituted with an alkoxy, cycloalkyl, alkylthio, aryloxy, or heteroaryloxy group as defined above.

For purposes of this invention "arylalkoxy," "alkoxyalkoxy," "alkylthioalkoxy," and "heteroarylalkoxy" denote an alkoxy group as defined above that is further substituted with an aryl, alkoxy, alkylthio, or heteroaryl group as defined above.

For purposes of this invention "arylthio" and "heteroarylthio," denote a thio group that is further substituted with an aryl or heteroaryl group as defined above.

For purposes of this invention "arylthioalkyl" and "heteroarylthioalkyl" denote an alkyl group as defined above that is further substituted with an arylthio or heteroarylthio group as defined above.

For purposes of this invention the term "arylalkylthio" is defined as aryl-C1–C8-alkyl-S—; "heteroarylalkylthio" is defined as heteroaryl-C1–C8-akyl-S—, where aryl and heteroaryl are as defined above.

For purposes of this invention "aryloxyalkylthio" is defined as aryloxy-C1–C8-alkyl-S; "heteroaryloxyalkylthio" is defined as heteroaryloxy-C1–C8-alkyl-S—; where aryloxy, heteroaryloxy, and alkyl are defined above.

For purposes of this invention "phenylalkynyl" is an alkynyl group further substituted with a phenyl group.

In the most preferred embodiment of this invention a substituted methyl comprises a methyl substituent further substituted with for example a furanyl group. In another embodiment of this invention a furanyl substituent is further substituted with a methyl group.

In a preferred embodiment of this invention trifluoromethoxy includes but is not limited to CF$_3$O—. In another embodiment of this invention trifluoromethylthio includes but is not limited to CF$_3$S—.

In one embodiment of this invention trifluoroethoxy is CF$_3$CH$_2$O—. In another embodiment of this invention trifluoroethylthio is CF$_3$CH$_2$S—.

The terms "monoalkylamino" and "dialkylamino" refer to moieties with one or two alkyl groups wherein the alkyl chain is 1 to 8 carbons and the groups may be the same or different. The terms monoalkylaminoalkyl and dialkylaminoalkyl refer to monoalkylamino and dialkylamino moieties with one or two alkyl groups (the same or different) bonded to the nitrogen atom which is attached to an alkyl group of 1 to 8 carbon atoms.

"Acyl" is a radical of the formula —(C=O)-alkyl or —(C=O)-perfluoroalkyl wherein the alkyl radical or perfluoroalkyl radical is 1 to 7 carbon atoms; preferred examples include but are not limited to, acetyl, propionyl, butyryl, trifluoroacetyl.

For purposes of this invention alkylsulfinyl is a R'SO— radical, where R' is an alkyl radical of 1–8 carbon atoms. Alkylsulfonyl is a R'SO$_2$— radical, where R' is an alkyl radical of 1–8 carbon atoms. Alkylsulfonamido, alkenylsulfonamido, alkynylsulfonamido are R'SO$_2$NH— radicals, where R' is an alkyl radical of 1–8 carbon atoms, an alkenyl radical of 2–8 carbon atoms, or an alkynyl radical of 2–8 carbon atoms, respectively.

Saturated or partially saturated heteroaryl groups are defined in this invention as heterocyclic rings selected from but not limited to the moieties; azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl.

The compounds of this invention contain one or more asymmetric carbon atoms and may thus give rise to stereoisomers, such as enantiomers and diastereomers. The stereoisomers of the instant invention are named according to the Cahn-Ingold-Prelog System. While the $C_1$ carbon of formula (A) is specified the present invention includes all the other possible stereoisomers; as well as the racemic mixtures and other mixtures of R and S stereoisomers (scalemic mixtures which are mixtures of unequal amounts of enantiomers) and pharmaceutically acceptable salts thereof. It should be noted that stereoisomers of the invention having the same relative configuration at a chiral center may nevertheless have different R and S designations depending on the substitution at the indicated chiral center.

For compounds of this invention containing two chiral centers, four possible stereoisomers are possible; these four stereoisomers are classified as two racemic pairs of diastereomers. These compounds of the invention may be present as racemic diastereomers which would be designated following the convention described in the 1997 Chemical Abstracts Index Guide, Appendix IV (Columbus, Ohio) whereas the first cited chiral atom is designated R* and the next cited chiral atom is designated R* if it possesses the same chirality as the first cited stereocenter or S* if it possesses opposite chirality to the first cited stereocenter. Alternatively, these compounds of the invention may be present as non-racemic mixtures of two diastereomers owing to the existence of a predefined stereocenter. In these instances, the predefined stereocenter is assigned based on the Cahn-Ingold-Prelog System and the undefined stereocenter is designated R* to denote a mixture of both R and S stereoisomers at this center. Compounds of this invention which possess two chiral centers but which are present as single stereoisomers are described using the Cahn-Ingold-Prelog System.

Based on the chiral center at the $C_1$ carbon position, a preferred embodiment of the instant invention is the compound of formula A(a) shown below:

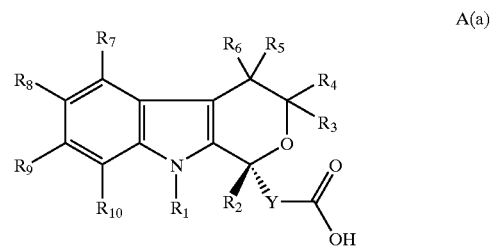

A(a)

The configuration at $C_1$ in Formula A(a) for purposes of this invention is also referred to as "isomer A", and the opposite configuration at $C_1$ is herein defined as "isomer B" and has the formula A(b) shown below:

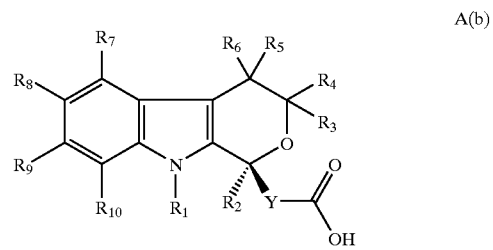

A(b)

In one embodiment of this invention the compound of the invention is comprised of a ratio of isomer A to isomer B of greater than 1:1. In the most preferred embodiment the compound is comprised of 100% isomer A. In further embodiments the compound is comprised of a ratio of isomer A to isomer B of at least about 9:1. In another embodiment the compound is comprised of a ratio of isomer A to isomer B of at least about 8:1. Additionally the compound is comprised of a ratio of isomer A to isomer B of at least about 7:1.

Pharmaceutically acceptable salts of the compounds of formula (I) having acidic moieties at $R_3$, $R_4$, $R_5$, $R_6$, $R_7$, $R_8$, $R_9$, or $R_{10}$ may be formed from organic and inorganic bases. For example alkali metal salts: sodium, lithium, or potassium and N-tetraalkylammonium salts such as N-tetrabutylammonium salts. Similarly, when a compound of this invention contains a basic moiety at $R_3$, $R_4$, $R_5$, $R_6$, $R_7$, $R_8$, $R_9$, or $R_{10}$, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

The compounds are preferably provided orally or subcutaneously. The compounds may be provided by intralesional, intraperitoneal, intramuscular or intravenous injection; infuision; liposome-mediated delivery; topical, nasal, anal, vaginal, sublingual, uretheral, transdermal, intrathecal, ocular or otic delivery. In order to obtain consistency in providing the compound of this invention it is preferred that a compound of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage to administer.

The compounds of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, such compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of the present invention may be delivered together with suitable diluents, preservatives, solubilizers, emulsifiers, adjuvants and/or carriers useful in treatment or prevention of Hepatitis C viral infection. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound capable of treating or preventing a Hepatitis C viral infection.

The compound of the present invention may be delivered locally via a capsule that allows a sustained release of the compound over a period of time. Controlled or sustained release compositions include formulation in lipophilic depots (for example, fatty acids, waxes, oils).

For purposes of this invention a chiral amine comprises a nitrogen atom in a three-membered ring connected to another atom bearing an unshared pair of electrons and may be, but is not limited to, ephedrine hemihydrate or cinchomine.

Another embodiment of this invention is where R2 of formula (A) is a sec-butyl group. In a preferred embodiment, the chiral carbon of the sec-butyl group has an S to R configuration ratio of 1:1. In further embodiments, the chiral carbon of the sec-butyl group has an S to R configuration ratio selected from the group consisting of at least 7:1, at least 8:1, and at least 9:1. In a most preferred embodiment of the invention, the chiral carbon of the sec-butyl group has 100% S configuration.

The following experimental details are set forth to aid in an understanding of the invention, and are not intended, and should not be construed, to limit in any way the invention set forth in the claims that follow thereafter.

DETAILED DESCRIPTION OF THE INVENTION

The compounds and compositions of the present invention can be readily prepared according to the following reaction schemes or modification thereof. It is also possible to make use of variants of these steps, which in themselves are known to and well within the preparatory skill of the medicinal chemist. Optically active isomers may be prepared, for example, by resolving racemic derivatives or by asymmetric synthesis. The resolution can be carried out by methods known to those skilled in the art such as in the presence of a resolving agent, by chromatography, or combinations thereof.

The compounds of the present invention can be synthesized as described in the schemes below (Schemes 1–4).

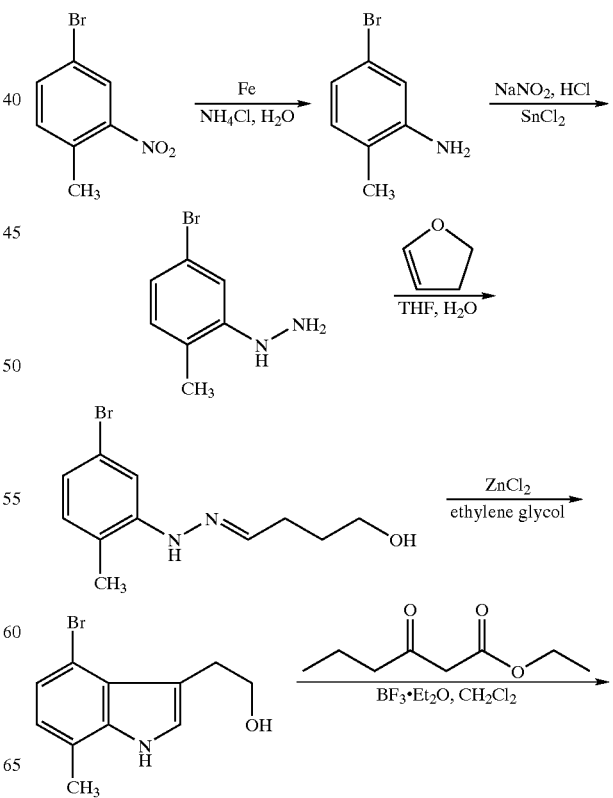

Scheme 1

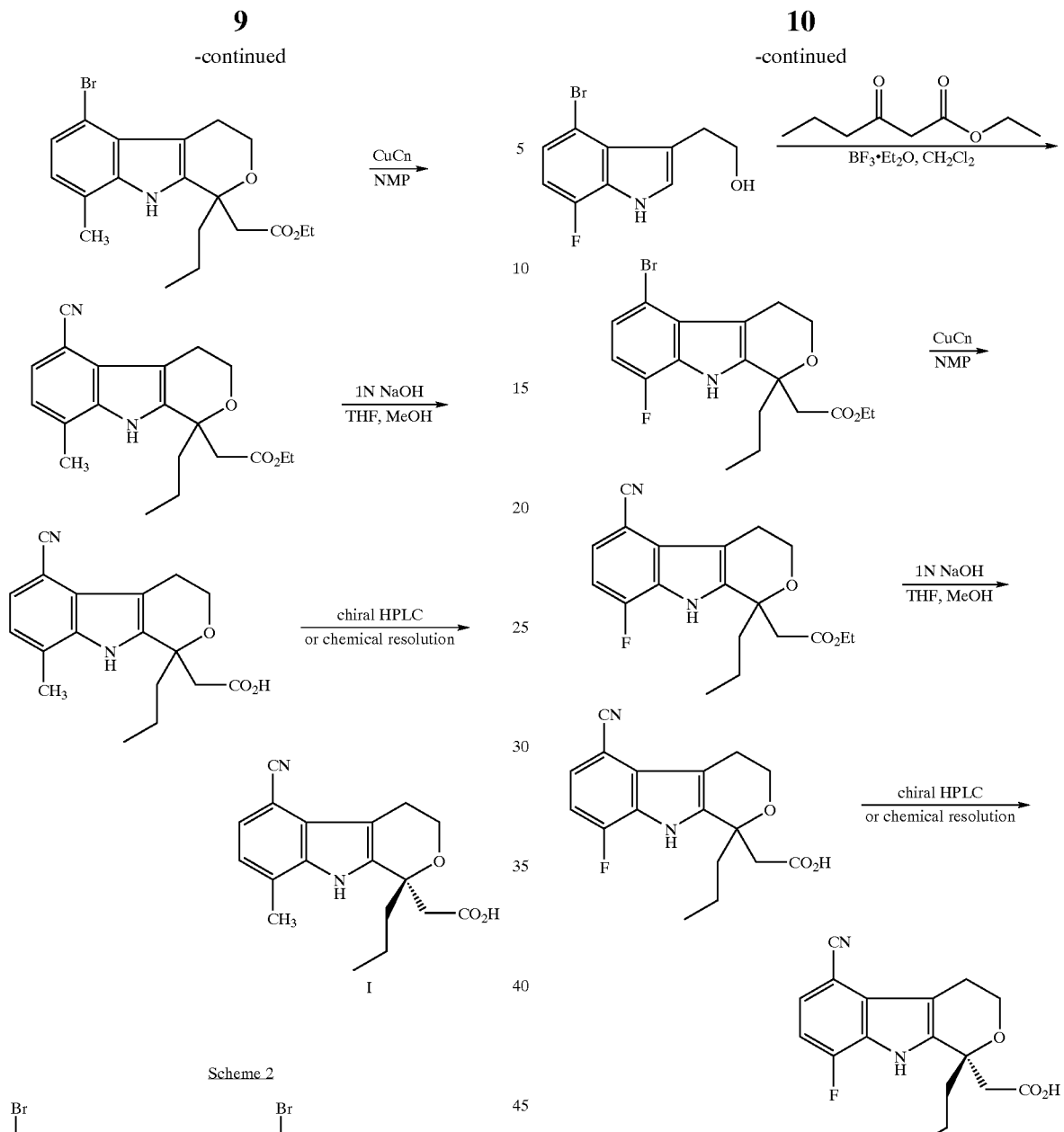
Scheme 2
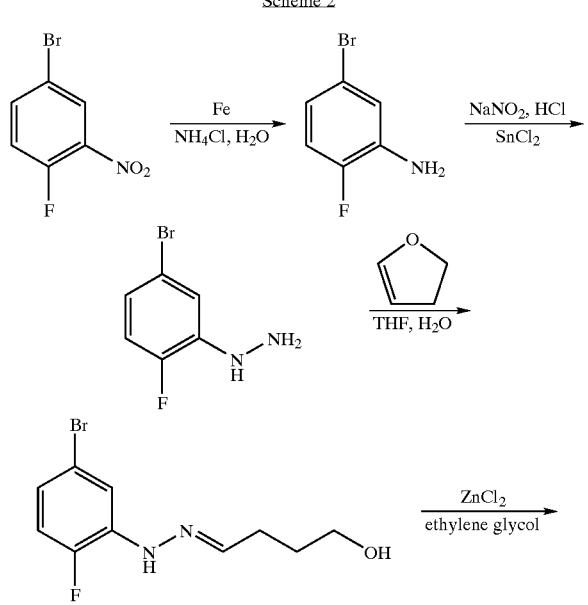
Scheme 3
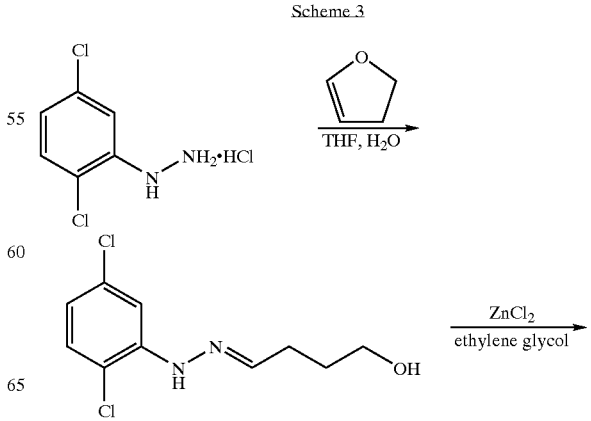

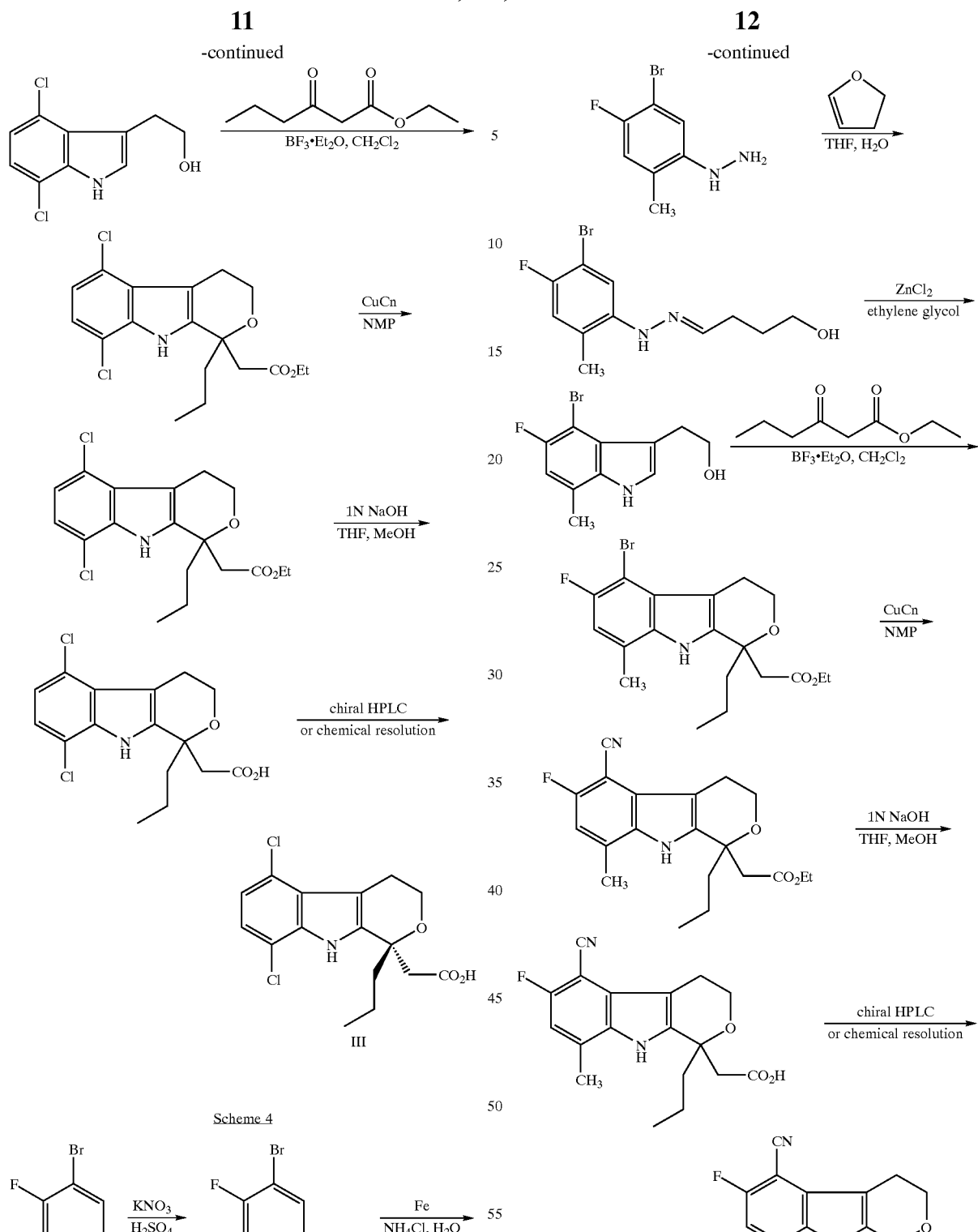
The ability of the compounds of the present invention to inhibit Hepatitis C Polymerase was established by the following experimental procedure:
NS5B from the BK strain (1b subtype) is expressed in *E. coli* as a protein in which the 21 C-terminal amino acids are replaced with a short linker and a hexahistidine tag (GSHHHHHH). The purified protein is mixed with radioactive nucleotides and allowed to replicate a heteropolymeric RNA substrate, primed by an endogenous short hairpin, resulting in an approximately 760 nt product. The radioactive product is captured on a filter and quantitated after removal of the unincorporated nucleotides.

Reagents:

10 mM uridine 5'-triphosphate (UTP) (Promega # p116B)
10 mM adenine 5'-triphosphate (ATP) (Promega # p113B)
10 mM cytidine 5'-triphosphate (CTP) (Promega # p114B)
10 mM guanine 5'-triphosphate (GTP) (Promega # p 115B)
boveine Serum Albumin (BSA) 10 mg/ml NEB (100× at 10 mg/ml) #007-BSA
RNasein (Promega #N251X) 40 U/ul
$^{33}$P-GTP (NEN-easytides NEG/606H 3000 Ci/mmol, 370 MBq/ml, 10 mCi/ml)
Falcon polypropylene 96 well plates (Becton Dickinson # 351190)
Millipore Multiscreen assay system-96 well-filtration plate #MADE NOB 50
Optiphase Supermix (Wallac) formulated by Fisher
Millipore Multiscreen liner for use in microbeta 1450-106 casette (Wallac) Perkin Elmer #1450-433
1 M (N-[2-hydroxyethyl]piperazine-N'-[2-ethanesulfonic acid]) HEPES, pH 7.3
Amersham Pharmacia Biotec (US16924-500 ml)
1 M $MgCl_2$ (SIGMA #M1028)
Dithiothreitol (DTT) (solid) (SIGMA # D9779)
RNase free water (GIBCO-BRL #10977-023)
Dimethyl sulfoxide (Aldrich #27685-5)
Basilen Blue (Sigma, B5520)
0.5M ethylenediaminetetraacetic acid (EDTA), pH 8 (GIBCO-BRL #15575-020)
Dibasic sodium phosphate 7 hydrate ($Na_2HPO_4.7H_2O$; Baker#3824-07)
Phosphoric acid (Baker, #0262.02)

Further Reagent Preparation:

0.5 M Na Phosphate buffer. Per liter, weigh 134 gr $Na_2HPO_4.7H_2O$, add water to 900 ml. Adjust pH to 7.0 with phosphoric acid. Top off with water to 1 L.

Dilute nucleotides 1:1000 to 10 μM (GTP and CTP) or 1:100 to 100 μM (ATP and UTP) into RNA-se free water.

Procedure:

(1) Compounds 10 μl at 10 μg/ml in 15% dimethylsulfoxide (DMSO)

When starting from 100 μg/ml compound stock in 1% DMSO:

Dispense 5 μl 30% DMSO per well
Dispense 5 μl compound (100 μg/ml) per well.

When starting from 50 μg/ml compound stock in 15% DMSO:

Add 10 μl compound per well.

(2) Enzyme Mix:

| Stock | Final Conc (in 50 μl assay volume) | Per 20 μl mix (1 reaction) | Per 600 reactions |
|---|---|---|---|
| DEPC $H_2O$ | | 17.06 μl | 10236 μl |
| 1 M HEPES, pH 7.5 | 20 mM | 0.5 μl | 300 μl |
| 1 M $MgCl_2$ | 5 mM | 0.25 μl | 150 μl |
| 100 mM DTT | 1 mM | 0.5 μl | 300 μl |
| 100 μM UTP | 0.5 μM | 0.25 μl | 150 μl |
| 100 μM ATP | 1 μM | 0.5 μl | 300 μl |
| 10 μM CTP | 0.08 μM | 0.4 μl | 240 μl |
| 10 μM GTP | 0.025 μM | 0.125 μl | 75 μl |
| BSA, 10 mg/ml | 0.05 mg/ml | 0.25 μl | 150 μl |
| HCV RdRp NS5B $d_{21}$BK (500 μg/ml or ~7.5 μM) | 24 nM | 0.16 μl | 96 μl |
| Total: | | 20 μl | 12 ml |

Add 20 μl enzyme mix into each well of the assay plate. Incubate compound and enzyme at room temperature for 15 minutes.

(3) Template Mix—Prepare Ahead

Spin down a tube of RNA (5 μg/tube stored in 75% ethanol and 0.3 M sodium acetate) in a microcentrifuge for 20 minutes. at 4° C. One tube is enough for 1–1.5 plates. Remove as much ethanol from the tube as possible by inverting the tube. Be gentle, pellet RNA may not adhere to the tube. Vacuum dry the RNA. Resuspend the RNA by adding 1 ml of DEPC water, close the cap of the tube tightly. To dissolve RNA, incubate RNA solution on ice for ~60 minutes and gently vortex. Spin briefly to ensure all RNA solution is down to the bottom of the tube before opening cap. Gently transfer RNA solution into a 5 ml or larger tube. Add another 3 ml of DEPC water (total 4 ml of volume). Add the following volumes of reagents

| Stock | Final concentration | Per 20 μl mix (1 reaction) | Per 600 reactions |
|---|---|---|---|
| RNAse-free water | | 2.98 μl | 1788 μl |
| Hepes, 1 M | 20 mM | 0.5 μl | 300 μl |
| RNase Inhibitor (40 μ/μl) | 0.4 U/μl | 0.5 μl | 300 μl |
| $^{33}$P-GTP 3000 Ci/mmol, 10 μCi/μl (3.3 μM) | 0.025 μM | 0.0125 μl | 7.5 μl |
| POF | 3 nM | 16 μl | 9600 μl |

Add 20 μl template mix per reaction (i.e. 20 ng of pOF per reaction or ~3 nM)

(4) Incubate reaction at room temperature (22–25° C.) for 2 hours.

(5) Stop reaction by adding 50 μl of 170 mM EDTA. Final concentration of EDTA is 85 mM.

(6) Prewet filters of Millipore multiscreen assay plate by adding 200 μl of 0.5 M sodium phosphate buffer, pH 7.0 into each well. Let stand at room temperature for 2–3 minutes.

(7) Place the multiscreen filter plate onto a Millipore Manifold and turn on vacuum to allow buffer to flow through. Turn off vacuum. Transfer 80 μl of the reaction product into each well of the filter plate. Let stand for 2–3 minutes. Turn on vacuum to filter reaction product.

(8) Turn off vacuum. Add. 200 μl of 0.5 M sodium phosphate buffer, pH 7.0 into each well to wash filter. Turn on vacuum. Repeat step (8) three more times.

(9) Remove polypropylene bottom. Spot dry filter at the bottom with paper towel. Air dry filter plate on a bench for 1 hour. Add 40 μl Super Mix scintillant. Seal top of the plate with a tape. Place plate into a Packard carrier or micro-beta carrier.

(10) Count plate using a Packard Topcount or micro-beta counter. Program 10 for $^{33}$P in Top count or $^{33}$P program in micro-beta.

Percent inhibition is calculated after background subtraction as a percent reduction of activity relative to the positive control (average value of the plate excluding the negative controls). For the primary screen hits were chosen as showing ≧75% inhibition.

See, Ferrari et al. 1999, J. Virology 73:1649–1654: "Characterization of soluble Hepatitis C virus RNA-dependent RNA polymerase expressed in *E. coli*" and Takamizawa et al 1991, J. Virology 65:1105–1113: "Structure and characterization of the Hepatitis C virus genome isolated from human carriers, both are hereby incorporated by reference."

The compounds of the present invention inhibited Hepatitis C polymerase as summarized in Table 1:

TABLE 1

| Example | HCV pol IC50 (μM) |
|---|---|
| 1 | 0.33 |
| 2 | 0.44 |
| 3 | 0.06 |
| 4 | 0.08 |

The ability of the compounds of the present invention to inhibit Hepatitis C virus replicon constitutively expressed in a human liver cell line was established by the following experimental procedure:

Clone A cells (licensed from Apath, LLC) are derived from Huh-7 cells (human hepatoma cell line) and constitutively express of the HCV replication proteins with concomitant amplification the HCV replicon (1b) genome. Cells are maintained and passaged in DMEM/10% FCS/1 mg/ml G418 (Geneticin from Gibco #11811-023; other media components as described below in "elisa media"). Care should be taken to maintain cell monolayers at a subconfluent state by 1:3 or 1:4 passages every 3–4 days. The replicon is extremely sensitive to the cellular metabolism/proliferation state and replicon copy number will rapidly decline in confluent monolayers (resting cells). Under ideal conditions each cell has, on average, 1000 copies of the HCV replicon genome.

Reagents:
Elisa Media:
Dulbecco's Modified Eagle Media (DMEM) (Gibco #12430-047)
2% Fetal Calf Serum (FCS) (HyClone #SH30070.03)
1× pen/strep (Gibco #15140-122)
1× non-essential amino acids (NEAA) (Gibco #11140-050)
no G418
Glutaraldehyde (Fisher #02957-4)
TWEEN-20, 10% (Roche #1332465)
TRITON X-100 (Sigma #T-8787)
Superblock in PBS (Pierce #37515)
NS5a monoclonal antibody (Virostat #1873)
Goat antimouse-HRP monoclonal antibody (BioRad #172-1011)
3,3',5,5' tetramethylbenzidine (TMB) substrate (Sigma #T-0440)
Compound Dilution/Cell Plating:
Drug Plate Preparation (Mother Plate)
10 μl of compounds (in DMSO) are added to column 3 of the mother plate. 5 μl of DMSO are added to the remaining columns. Mother plates are set aside until ready for serial dilution to be performed.
Control Drugs
Drug and Cell Addition:
The process for each plate involves:
Prepare cell plates (daughter plates) by adding 52 μl of Elisa media to each well.
In Mother plates, serially transfer 50 μl/well from column 3 through column 12.
Transfer 8 μl from mother plate to daughter plates (all 96 wells).
Place daughter plates in incubator until cells are prepared.
Harvest Clone A cells and plate directly into daughter plates at 0.7×10$^5$ cells/ml, 100 μl/well.
All plates are incubated at 37° C. in 5% $CO_2$ for 3 days.
Elisa Assay:
Remove media from 96-well plates (cells should be ca 80% confluent) by flicking into sink.
Add 130 ul/well 1× PBS+0.05% glutaraldehyde.
Incubate 37° C. for 1 hour.
Remove by flicking into sink.
Wash 3× with 300 μl/well PBS, shaking for 5 minutes each wash. Remove by flicking into sink.
Add 130 μl/well PBS+0.05% TWEEN-20+0.1% TRITON X-100.
Incubate 37° C. for 10 minutes.
Remove by flicking into sink.
Add 300 μl/well Superblock in PBS.
Incubate 37° C. for 1 hour.
Remove by flicking into sink.
Wash 3× with 300 μl/well PBS, shaking 5 minutes each wash. Remove by flicking into sink.
During last wash, make a 1:100 dilution of NS5a Monoclonal-antibody (Mab) in
Superblock+0.02% TWEEN-20.
After last wash, add 50 μl/well diluted Mab.
Incubate 37° C. for 1 hour.
Remove by flicking into sink.
Wash 3× with 300 μl/well PBS+0.02% TWEEN-20, shaking 5 minutes each wash.
Remove by flicking into sink.
During last wash, make a 1:500 dilution of goat antimouse-HRP Mab in
Superblock+0.02% TWEEN-20.
After last wash, add 50 μl/well diluted Mab.
Incubate 37° C. for 1 hour.
Remove by flicking into sink.
Wash 5× with 300 μl/well PBS+0.02% TWEEN-20, shaking 5 minutes each wash. Remove by flicking into sink.
Wash 3× with 300 μl/well PBS, shaking 5 minutes each wash. Remove by flicking into sink.
After last wash, add 130 μl/well room temperature TMB substrate.
Incubate until blue color developes.
Add 130 μl/well IN HCl to stop reaction (color turns from blue to yellow).
Read plates with O.D. 450 filter.
ANALYSIS OF RESULTS: IC50 (uM); IC50 (ug/ml); % Inhibition
REFERENCE COMPOUNDS: Interferon-a2; 4–30 U/ml IC50

The following non-limiting specific examples are included to illustrate the synthetic procedures used for preparing compounds of the Formula (A). In these examples, all chemicals and intermediates are either commercially available or can be prepared by standard procedures found in the literature or are known to those skilled in the art of organic synthesis.

EXAMPLE 1

[(R)-5-cyano-8-methyl-1-propyl-1,3,4,9-tetrahydropyrano[3,4-b]indol-1-yl]acetic acid 5-Bromo-2-methylaniline The mixture of iron powder (9.31 g, 167 mmol) and $NH_4Cl$ (2.48 g, 46.3 mmol) in water (50 mL) was refluxed for 30 minutes. To this hot mixture was added 4-bromo-2-nitrotoluene (10 g, 46.3 mmol) slowly and then the reaction mixture was refluxed for 48 hours. The mixture was cooled to room temperature and extracted with EtOAc (3×100 mL). The organic solution was washed with H$_2$O (3×200 mL) and brine (200 mL), dried (Na$_2$SO$_4$), and concentrated. The residue was purified by flash chromatography (silica, 15% EtOAc in hexanes) to give 7.9 g (92%) of title compound as a pale yellow oil. $^1$H nuclear magnetic resonance (NMR) (CDCl$_3$): 300 MHz δ 6.88 (m, 1H), 6.81 (m, 2H), 3.63 (bs, 2H), 2.09 (s, 3H).

5-Bromo-2-methylphenylhydrazine Hydrochloride

To a suspension of 5-bromo-2-methylaniline (4.80 g, 25.8 mmol) in concentrated HCl (16 mL) was added dropwise a solution of sodium nitrite (1.96 g, 28.4 mmol) in water (10 mL) over 30 minutes at 0° C. To the mixture was added dropwise a solution of SnCl$_2$.2H$_2$O (17.46 g, 77.4 mmol) in concentrated HCl (15 mL) over 50 minutes. After stirring for 1 hour at 0° C., the reaction mixture was basified with 50% NaOH (30 mL). The mixture was further diluted with water (20 mL) and treated with another 50% NaOH (10 mL) and then crushed ice (100 g). The reaction mixture was extracted with ether (3×100 mL) and the combined organic phases were washed with brine, dried over Na$_2$SO$_4$, and filtered. The filtrate was acidified by adding an anhydrous solution of HCl in ether (1 N in ether, 31 mL, 31 mmol). The precipitate was collected and dried under reduced pressure to give 4.57 g (75%) of title compound as a white amorphous solid. $^1$H NMR (DMSO): 300 MHz δ 10.31 (bs, 3H), 8.11 (bs, 1H), 7.12 (s, 1H), 7.06 (m, 2H), 2.14 (s, 3H).

4-Bromo-7-methyl Tryptophol

To a solution of 5-bromo-2-methylphenylhydrazine hydrochloride (4.57 g, 19.2 mmol) in 30% aqueous tetrahydrofuran (THF) (100 mL) at 0° C. was added dropwise a solution of 2,3-dihydrofuran (1.60 mL, 21.2 mmol) in THF (10 mL). After stirring for 2 h at 0° C. and 12 hours at room temperature, the reaction mixture was diluted with ether (100 mL). The organic solution was washed with saturated NaHCO$_3$ (2×100 mL) and brine (100 mL), dried (Na$_2$SO$_4$) and concentrated. The residue was dissolved in ethylene glycol (30 mL), treated with ZnCl$_2$ (5.76 g, 42.2 mmol), and heated at 170° C. for 4 hours. The reaction mixture was cooled down to room temperature and 6 N HCl (100 mL) was added. The mixture was extracted with ether (3×100 mL) and washed with water (200 mL) and brine (200 mL). The organic solution was dried over Na$_2$SO$_4$ and concentrated. The residue was purified by flash chromatography (silica, 40% EtOAc in hexanes) to give 1.22 g (25%) of title compound as a light brown oil. $^1$H NMR (CDCl$_3$): 300 MHz δ 8.23 (bs, 1H), 7.18 (d, J=7.65 Hz, 1H), 7.08 (d, J=2.16 Hz, 1H), 6.81 (d, J=7.65 Hz, 1H), 3.95 (t, J=6.42 Hz, 2H), 3.27 (t, J=6.42 Hz, 2H), 2.40 (s, 3H), 1.69 (bs, 1H).

5-Bromo-8-methyl-1-propyl-1,3,4,9-tetrahydropyrano[3,4-b]indole-1-acetic Acid Ethyl Ester To a solution of 4-bromo-7-methyl tryptophol (1.12 g, 4.41 mmol) and ethyl butyrylacetate (0.71 mL, 4.41 mmol) in CH$_2$Cl$_2$ (20 mL) was added BF$_3$.OEt$_2$ (0.56 mL, 4.41 mmol) dropwise at room temperature. The solution was stirred for 2 hours and then washed with saturated aqueous NaHCO$_3$ (15 mL) and brine (15 mL). The organic phase was dried (Na$_2$SO$_4$) and filtered through a pad of silica gel. The filter cake was washed with additional CH$_2$Cl$_2$ and the combined organic layer was evaporated to provide 1.62 g (93%) of title compound as a white solid. $^1$H NMR (CDCl$_3$): 300 MHz δ 9.33 (bs, 1H), 7.11 (d, J=7.65 Hz, 1H), 6.76 (d, J=7.65 Hz, 1H), 4.19 (m, 2H), 4.03 (m, 1H), 3.90 (m, 1H), 3.15 (m, 2H), 3.03 (d, J=16.6 Hz, 1H), 2.89 (d, J=16.6 Hz, 1H), 2.43 (s, 3H), 2.08 (m, 1H), 1.96 (m, 1H), 1.38 (m, 1H), 1.27 (t, J=7.14 Hz, 3H), 1.18 (m, 1H), 0.87 (t, J=7.29 Hz, 3H).

5-Cyano-8-methyl-1-propyl-1,3,4,9-tetrahydropyrano[3,4-b]indole-1-acetic Acid Ethyl Ester 5-Bromo-8-methyl-1-propyl-1,3,4,9-tetrahydropyrano[3,4-b]indole-1-acetic acid ethyl ester (1.27 g, 3.22 mmol) and CuCN (0.433 g, 4.83 mmol) was dissolved in N-methyl-2-pyrrolidinone (15 mL) and the solution was divided into 4 microwave reaction vessels (3.75 mL each). The reaction vessels were heated in microwave at 220 ° C. for 15 minutes. The reaction mixtures in 4 vessels were combined and then diluted with water (30 mL). The crude mixture was extracted with EtOAc (3×50 mL). The combined organic phase was washed with brine (100 mL), dried over Na$_2$SO$_4$ and concentrated. The residue was purified by flash chromatography (silica, 20% EtOAc in hexanes) to give 0.959 g (88%) of title compound as a white solid. $^1$H NMR (CDCl$_3$): 300 MHz δ 9.75 (bs, 1H), 7.33 (d, J=7.52 Hz, 1H), 6.93 (d, J=7.52 Hz, 1H), 4.21 (m, 2H), 4.11 (m, 1H), 4.03 (m, 1H), 3.08 (t, J=5.52, 2H), 2.99 (d, J=4.17 Hz, 2H), 2.57 (s, 3H), 2.06 (m, 2H), 1.42 (m, 1H), 1.26 (t, J=7.16 Hz, 3H), 1.18 (m, 1H), 0.88 (t, J=7.32 Hz, 3H).

5-Cyano-8-methyl-1-propyl-1,3,4,9-tetrahydropyrano[3,4-b]indole-1-acetic Acid

To a solution of 5-cyano-8-methyl-1-propyl-1,3,4,9-tetrahydropyrano[3,4-b]indole-1-acetic acid ethyl ester (0.959 g, 2.82 mmol) in THF/MeOH (7 mL/15 mL) was added 1 N NaOH (5.64 mL, 5.64 mmol). The reaction mixture was stirred at ambient temperature overnight. Most of THF/MeOH was removed under reduced pressure and the resulting mixture was acidified with 1 N HCl. The mixture was extracted with EtOAc (3×30 mL). The combined organic phase was washed with brine (60 mL), dried over Na$_2$SO$_4$ and concentrated to provide 0.868 g (99%) of title compound as a white solid. $^1$H NMR (acetone-d$_6$): 300 MHz δ 10.37 (bs, 1H), 7.35 (d, J=7.50 Hz, 1H), 7.03 (d, J=7.50 Hz, 1H), 4.05 (m, 2H), 3.08–2.91 (m, 4H), 2.54 (s, 3H), 2.09 (m, 2H), 1.45 (m, 1H), 1.03 (m, 1H), 0.84 (t, J=7.26 Hz, 3H).

[(R)-5-cyano-8-methyl-1-propyl-1,3,4,9-tetrahydropyrano[3,4-b]indol-1-yl]acetic acid Preparative HPLC using CHIRALPACK-AD (250×20 mm) and 10% isopropyl alcohol in heptane (0.1% trifluoroacetic acid (TFA)) as eluant gave (R) and (S) enantiomers of 5-cyano-8-methyl-1-propyl-1,3,4,9-tetrahydropyrano[3,4-b]indole-1-acetic acid as white solids. HRMS (ES]) [M+H]$^+$ calculated for C$_{18}$H$_{21}$N$_2$O$_3$ 313.1547, found 313.1545 (R enantiomer) and 313.1547 (S enantiomer); Chiral HPLC HP 1100 with spiderlink CHIRALPACK-AD, 250×4.6 mm, isopropyl alcohol/heptane containing 0.1% TFA (10:90), 1.0 mL/minutes, DAD 215 nm; t$_R$=6.98 minutes (R enantiomer), 9.37 minutes (S enantiomer).

Alternatively, [(R)-5-cyano-8-methyl-1-propyl-1,3,4,9-tetrahydropyrano[3,4-b]indol-1-yl]acetic acid can be obtained by resolution with cinchonine according to the following procedure. (±)-5-Cyano-8-methyl-1-propyl-1,3,4,9-tetrahydropyrano[3,4-b]indole-1-acetic acid (6.4 g, 20.5 mmol) and cinchonine (5.9 g, 20.0 mmol) were dissolved in a mixture of 2-butanone (125 mL) and water (5 mL) with heating. The clear solution was stirred and allowed to cool to room temperature overnight. The resulting solid was isolated, washed with 10 mL of 2-butanone, and dried to give 2.4 g (20% yield, >98% e.e.). The mother liquor was concentrated and dissolved again in a mixture of 2-butanone (100 mL) and water (1.5 mL) with heating. The solution was stirred and allowed to cool to room temperature overnight. The resulting solid was isolated, washed with 10 mL of 2-butanone, and dried to give a second crop of salt: 2.3 g (18% yield, >98% e.e.). The two crops (total 4.7 g) were combined and treated with 50 mL of 1N HCl and 100 mL of ethyl acetate. The ethyl acetate layer was washed with 1N HCl (30 mL) and water (50 mL). The aqueous layers were combined and extracted with ethyl acetate (50 mL). This ethyl acetate layer was washed with water (50 mL). The combined ethyl acetate layers were dried over sodium sulfate, filtered, and concentrated in vacuo to give 2.25 g. This material was triturated with 10 mL of ethyl acetate and the precipitate was collected, rinsed with 5 mL of ethyl acetate, and dried to give 1.27 g (e.e. >98%). The mother liquor was concentrated to a volume of 5 mL and the newly formed precipitate was collected, rinsed with 2 mL of ethylacetate and dried. A second crop of 0.4 g was obtained with an e.e. of >99%. The mother liqour was concentrated and gave a third crop of 0.5 g with an e.e. of >99%.

The absolute configuration of the compound of Example 1 was determined by single crystal X-ray crystallography of the 4-bromobenzyl amide derivative, which was prepared as described below.

1-(R)-N-(4-Bromo-benzyl)-2-(5-cyano-8-methyl-1-propyl-1,3,4,9-tetrahydropyrano[3,4-b]indol-1-yl)-acetamide To a solution of 1-(R)-5-cyano-8-methyl-1-propyl-1,3,4,9-tetrahydropyrano[3,4-b]indole-1-acetic acid (20.0 mg, 0.064 mmol), 1-[3-(dimethylamino)propyl]-3-ethylcarbodiimide hydrochloride (EDCl, 15.0 mg, 0.077 mmol) and 1-hydroxybenzotriazole (10.4 mg, 0.077 mmol) in DMF (4 mL) was added N,N-diisopropylethylamine (67 µl, 0.384 mmol) followed by 4-bromobenzylamine hydrochloride (17.1 mg, 0.077 mmol) at room temperature. The reaction mixture was stirred for 20 hours at ambient temperature. Water (5 mL) was added to the mixture and the resulting mixture was extracted with EtOAc (3×10 mL). The combined organic phase was washed with brine (20 mL), dried over $Na_2SO_4$ and concentrated. The residue was purified by flash chromatography (silica, 40% EtOAc in hexanes) to give 27 mg (88%) of title compound as a white solid. The solid was crystallized from EtOAC for X-ray crystallography. Mp=173–175° C.; $^1$H NMR (CDCl$_3$): 300 MHz δ 10.15 (bs, 1H), 7.33 (m, 3H), 6.97 (m, 2H), 6.88 (m, 1H), 4.42 (dd, J=11.2, 4.6 Hz, 1H), 4.29 (dd, J=11.2, 4.6 Hz, 1H), 4.03 (m, 2H), 3.11–2.95 (m, 4H), 2.24 (s, 3H), 2.07 (m, 1H), 1.91 (m, 1H), 1.35 (m, 2H), 0.89 (t, J=5.4 Hz, 3H); HRMS (ESI) [M+H]$^+$ calculated for $C_{25}H_{27}BrN_3O_2$ 480.1281, found 480.1285.

EXAMPLE 2

[(R)-5-cyano-8-fluoro-1-propyl-1,3,4,9-tetrahydropyrano[3,4-b]indol-1-yl]acetic acid 5-Bromo-2-fluoroaniline Iron powder (9.3 g, 0.166 mM) and ammonium chloride (1.7 g, 0.032 mM) were stirred in water (42 ml) at 100° C. for 30 minutes. Commercially available 2-nitro 4-bromo fluorobenzene (9.2 g, 0.42 mM) was added drop wise to the above solution over a period of 45 minutes. The reaction was stirred at 100° C. for an additional five hours. Water was removed in vacuo. The resultant crude solution was stirred in ethyl acetate (100 mL) for 20 minutes and the organic solution was decanted off. This wash was repeated two more times. The organic layers were combined, dried (MgSO$_4$), passed through a plug of SiO$_2$, and concentrated to afford 4.2 g (53% yield) of the desired product as a red oil. The product was used without further purification. NMR (CHCl$_3$) δ 3.78 (bs, 2H); 6.65–7.07(m, 3H).

See, Courtin, A. Helv. Chim. Acta. 66, 1, (1983), hereby incorporated b reference.

5-Bromo-2-fluorophenylhydrazine

A solution of sodium nitrate (0.49 g, 0.007 mM) in water (1.5 ml) was added drop wise to a vigorously stirred heterogeneous solution of 5-bromo-2fluoroaniline (1.4 g) in concentrated HC(aq)(3.5 ml) over a 30 minutes period at 0° C. Tin (II) chloride dihydrate (4.5 g, 0.02 mM) in concentrated HCl(aq) (3.5 ml) was added drop wise to the above solution over a period of 30 minutes. After the addition, the solution was allowed to stir at 0° C. for one hour. The reaction solution was basified (pH>7) by slowly adding a solution of 50% aqueous NaOH to the reaction mixture. The water layer was washed with diethyl ether (3×). The organic layers were combined, dried (MgSO$_4$), and concentrated. The resultant solid was thoroughly washed with hexanes. The undissolved solid was captured on filter and further washed with hexanes to afford 0.81 g (54% yield) of the desired product as an off-white solid. NMR (CHCl$_3$) δ 5.45 (bs, 1H); 6.80–6.86(m, 2H); 7.25–7.28 (m, 1H).

See, McKittrick, B. et al., J. Heterocyclic Chem. 27, 2151 (1990), hereby incorporated by reference.

4-Bromo-7-fluoro Tryptophol 2,3 Dihydrofuran (2.0 ml, 0.026 mM) was added to a solution of 5-bromo-2-fluorphenyl hydrazine (4.43 g, 0.21 mM) in dry THF (40 ml) at 0° C. Concentrated HCl(aq) (2.0 ml) was added to the mixture and the reaction was allowed to warm to room temperature and stirred overnight. THF was removed in vacuo. The crude residue was taken up in water and washed with ethyl acetate (3×). The organic layers were combined, dried (MgSO$_4$), and concentrated to afford 4.2 g of a mixture of the mono and di-adducts as a red oil. This crude mixture was used without further purification in the next step.

Zinc chloride (5.4 g, 0.39 mM) and the crude mixture were stirred in ethylene glycol at 160° C. for three hours. The reaction was cooled and diluted with 10% HCl (aq) (50 ml). The aqueous layer was washed with ethyl acetate (3×). The organic layers were combined, dried (MgSO$_4$), and concentrated. The product was purified by using silica gel flash chromatography (mobile phase: 3:2/hexanes: ethyl acetate) to afford 1.2 g (yield: 21%) of the desired product as an off-white solid. NMR(CHCl$_3$) δ 3.26 (t, 2H, 6.3Hz); 3.96(t, 2H, 6.4Hz); 6.75 (m, 1H); 7.15(m, 2H); 8.54(bs, 1H).

5-Bromo-8-fluoro-1-propyl-1,3,4,9-tetrahydropyrano[3,4-b]indole-1-acetic Acid Ethyl Ester BF$_3$-etherate (0.74 ml, 0.0059 mM) was added to a solution of 4-bromo-7-fluorotryptophol (1.0 g, 0.0039 mM) and ethyl butyrylacetate (0.93 ml, 0.0059 mM) in dry dichloromethane (15 ml). This reaction was stirred for three hours at room temperature. Saturated NaHCO$_3$ (aq) (15 ml) was added to quench the reaction. The solution was washed with DCM (2×). The organic layers were combined, dried (MgSO$_4$), passed through a plug of SiO$_2$, and concentrated to afford 1.02 g (66% yield) of the desired product as an off-white solid. NMR (CHCl$_3$) δ 0.87 (t, 3H, 7.38Hz); 1.44(m, 1H); 1.28(t, 3H, 7.14Hz); 1.39(m, 1H); 1.93(m, 1H); 2.03(m, 1H); 2.91 m(m, 1H); 3.06(m 1H); 3.15(m, 2H), 3.91(m, 1H); 4.03(m, 1H), 4.22(m, 2H); 6.72(m, 1H); 7.09 (m, 1H); 9.50(s, 1H).

5-Cyano-8-fluoro-1-propyl-1,3,4,9-tetrahydropyrano [3,4-b]indole-1-acetic Acid Ethyl Ester The above ester (1.02 g, 0.026 mM) was dissolved in N-Methyl pyrrolidinone (12 ml). This solution was distributed equally into four Personal Chemistry microwave reaction vessels. CuCN (0.085 g, 0.0096 mM) was added into each reaction vessel. The reaction vessels were heated, under microwave conditions, at 220° C. for 15 minutes. The reaction solutions were combined and diluted with water (30 ml). The aqueous layer was washed with ethyl acetate (3×). The organic layers were combined, dried (MgSO$_4$), and concentrated. The product was purified by SiO$_2$ flash chromatography to afford 0.81 g (92% yield) of the desired product as an off-white solid. NMR (d₆-DMSO) δ 0.78 (t, 3H); 0.86(m, 2H); 1.0(t, 3H); 1.29(m, 2H); 1.92(m, 2H); 2.76(d, 1H); 2.86(t, 2H); 3.02(d, 1H); 3.9(m, 4H); 7.07(m, 1H); 7.5(m, 1H); 11.94(s, 1H).

5-Cyano-8-fluoro-1-propyl-1,3,4,9-tetrahydropyrano[3,4-b]indole-1-acetic Acid

1N NaOH(aq) (4.6 ml) was added to a solution of the above ester (0.8 g, 0.0023 mM) in 1:1/MeOH: THF (10 ml) and stirred at room temperature overnight. THF and MeOH were removed in vacuo. The residue was diluted with brine (10 ml), acidified with (pH<2) concentrated HCl(aq), and washed with ethyl acetate (3×). The organic layers were combined, dried (MgSO₄), and concentrated to afford 0.61 g (82% yield) of the desired product as a white solid. NMR (d₆-DMSO) δ 0.95 (t, 3H, 5.4Hz); 1.23(m, 1H); 1.42(m, 1H); 2.05(m, 1H); 2.99–3.13 (m, 4H); 3.99(m, 1H); 4.11(m, 2H); 6.90(m, 1H); 7.39(m, 1H); 9.45(s, 1H).

[(R)-5-cyano-8-fluoro-1-propyl-1,3,4,9-tetrahydropyrano[3,4-b]indol-1-yl]acetic acid Preparative HPLC using CHIRALPACK-AD (250×20 mm) and 10% isopropyl alcohol in heptane (0.1% TFA) as eluant gave (R) and (S) enantiomers of 5-cyano-8-fluoro-1-propyl-1,3,4,9-tetrahydropyrano[3,4-b]indole-1-acetic acid as white solids. Chiral HPLC HP 1100 with spiderlink CHIRALPACK-AD, 250×4.6 mm, isopropyl alcohol/heptane containing 0.1% TFA (10:90), 1.0 mL/minutes, DAD 215 nm; $t_R$=6.1 minutes (R enantiomer), 8.3 minutes (S enantiomer).

The absolute configuration of the compound of Example 2 was determined by single crystal X-ray crystallography of the 4-bromobenzyl amide derivative.

1-(R)-N-(4-Bromo-benzyl)-2-(5-cyano-8-fluoro-1-propyl-1,3,4,9-tetrahydropyrano[3,4-b]indol-1-yl)-acetamide The procedure described for Example 3 was followed starting from 1-(R)-5-cyano-8-fluoro-1-propyl-1,3,4,9-tetrahydropyrano[3,4-b]indole-1-acetic acid. 1H NMR (d₆-DMSO) δ0.79 (t, 3H, 5.4Hz); 0.94(m, 1H); 1.31(m, 1H); 1.96(m, 2H); 2.75 (d, 1H, 10.2Hz); 2.91(m, 3H); 4.03(m, 2H); 4.21(d, 2H, 4.5Hz); 7.09(m, 3H); 7.37(d, 2H, 6.0Hz); 7.52(m, 1H); 8.22(t, 1H, 6.0Hz); 11.93(s, 1H); MS: M-H: 482.1; CHN for $C_{24}H_{23}BrFN_3O_2$—Theory: C: 59.51, H: 4.79, N: 8.68 Found: C: 59.53, H: 4.86, N: 8.66.

EXAMPLE 3

[(R)-5,8-dichloro-1-propyl-1,3,4,9-tetrahydropyrano[3,4-b]indol-1-yl]acetic acid 4,7-Dichloro-Tryptophol To a solution of 2,5 dichlorophenylhydrazine hydrochloride (20.4 g 0.11 mol) in THF (80 mL) at 0° C. was added dropwise a solution of 2,3-dihydrofuran (10.5 mL, 0.14 mol), water (15 mL) and HCL concentrated (5 mL). After stirring for 4 hours, the reaction mixture was diluted with ether (100 mL). The organic solution was washed with saturated NaCl (2×50 mL) and dried (Na₂SO₄) and concentrated. The residue was dissolved in ethylene glycol (60 mL), treated with ZnCl₂ (34.6 g, 0.25 mol), and heated at 140° C. for 8 hours. The reaction mixture was cooled down to room temperature and 10% HCl was added. The mixture was extracted with ethyl actetate (3×75 mL) and washed with brine. The organic solution was dried over Na₂SO₄ and concentrated. The residue was purified by flash chromatography (silica gel 60, EtOAc:Hexane 3:1) to give 10.4 g (39%) of title compound as a light brown oil. ¹H NMR (CDCl₃): 300 MHz δ 8.35 (bs, 1H), 7.16 (d, J=2.1 Hz, 1H), 7.09 (d, J=8.4 Hz, IH), 7.01 (d, J=8.1 Hz, 1H), 3.95 (t, J=6.3 Hz, 2H), 3.25 (t, J=6.3 Hz, 2H), 1.49 (bs, 1H).

5,8 dichloro-1-propyl-1,3,4,9-tetrahydropyrano[3,4-b]indole-1-acetic Acid Ethyl Ester To a solution of 5,8 dichloro tryptophol (4.25 g, 18.55 mmol) and ethyl butyrylacetate (4.37 mL, 27.63 mmol) in CH₂Cl₂ (40 mL) was added BF₃.OEt₂ (3.50 mL, 27.63 mmol) dropwise at room temperature. The solution was stirred for 2 hours and then washed with saturated aqueous NaHCO₃ (30 mL) and brine and concentrated. The oil was then purified by flash chromatography (silica gel 60, EtOAc:Hexane 4:1) to yield 1.5 g (32%). ¹H NMR (CDCl₃): 300 MHz δ 9.55 (bs, 1H), 7.03 (d, J=8.10 Hz, 1H), 6.95 (d, J=8.10 Hz, 1H), 4.3 (m, 2H), 4.02 (m, 1H), 3.89 (m, 1H), 3.01 (m, 2H), 2.99 (m, 1H), 2.92(m, 1H), 2.01 (m, 2H), 1.28 (m, 5H), 0.88 (t, J=7.30 Hz, 3H).

5,8 dicholor-1-propyl-1,3,4,9-tetrahydropyrano[3,4-b]indole-1-acetic Acid

To a solution of 5,8 dicholoro-1-propyl-1,3,4,9-tetrahydropyrano[3,4-b]indole-1-acetic acid ethyl ester (1.2 g, 3.24 mmol) in EtOH (35 mL) was added 1 N NaOH (7 mL). The reaction mixture was stirred at 50° C. for 6 hours. Most of EtOH/NaOH was removed under reduced pressure and the resulting mixture was purified on HPLC to yield a white solid 0.730 g (66%). ¹H NMR (CDCl₃): 300 MHz δ 9.12 (bs, 1H), 7.03 (d, J=8.26 Hz, 1H), 6.96 (d, J=8.26 Hz, 1H), 4.04 (m, 2H), 3.14(m, 2H), 3.06(m, 2H), 2.03 (m, 2H), 1.42 (m, 1H), 1.21(m, 1H), 0.89 (t, J=7.34 Hz, 3H).

[(R)-5,8-dichloro-1-propyl-1,3,4,9-tetrahydropyrano[3,4-b]indol-1-yl]acetic acid Preparative HPLC using CHIRALCEL OJ (250×20 mm) and 3% isopropyl alcohol in heptane (0.1% TFA) as eluant gave (S) and (R) enantiomer of 5,8-dichloro-1-propyl-1,3,4,9-tetrahydropyrano[3,4-b]indole-1-acetic acid as a white solid. Chiral HPLC—HP 1100 with spiderlink; CHIRALCEL OJ, 250×4.6 mm, isopropyl alcohol/heptane (containing 0.1% TFA)=3:97, 1.0 mL/minutes, DAD 215 nm; $t_R$=10.2 minutes (S enantiomer), 15.7 minutes (R enantiomer).

EXAMPLE 4

[(R)-5-cyano-6-fluoro-8-methyl-1-propyl-1,3,4,9-tetrahydropyrano [3,4-b]indol-1-yl]acetic acid 4-Bromo-3-fluoro-6-nitrotoluene To a stirred solution of 4-bromo-3-fluorotoluene (10 g, 52.9 mmol) in H₂SO₄ (100 mL) was added KNO₃ (5.34 g, 52.9 mmol) at 0° C. After stirring overnight at room temperature, the reaction mixture was poured into ice (200 g) and extracted with EtOAc (3×300 mL). The organic solution was washed with brine (200 mL), dried (Na₂SO₄), and concentrated to give 12.35 g (100%) of title compound as a pale yellow oil. ¹H NMR (CDCl₃): 300 MHz δ 8.29 (d, J=6.30 Hz, 1H), 7.12 (d, J=8.61 Hz, 1H), 2.60 (s, 3H).

5-Bromo-4-fluoro-2-methylaniline

The mixture of Iron powder (17.8 g, 318 mmol) and NH₄Cl (5.10 g, 95.4 mmol) in water (100 mL) was refluxed for 30 minutes. To this hot mixture was added 4-bromo-3-fluoro-6-nitrotoluene (18.6 g, 79.5 mmol) slowly and then the reaction mixture was refluxed for 48 hours. The mixture was cooled to room temperature and extracted with EtOAc (3×200 mL). The organic solution was washed with H₂O (3×300 mL) and brine (300 mL), dried (Na₂SO₄), and concentrated. The residue was purified by flash chromatography (silica, 20% EtOAc in hexanes) to give 11.7 g (72%) of title compound as a pale yellow solid. ¹H NMR (CDCl₃): 300 MHz δ 6.82 (m, 2H), 3.49 (bs, 2H), 2.11 (s, 3H).

5-Bromo-4-fluoro-2-methylphenylhydrazine Hydrochloride

To a suspension of 5-bromo-4-fluoro-2-methylaniline (11.2 g, 54.9 mmol) in concentrated HCl (35 mL) was added dropwise a solution of sodium nitrite (4.17 g, 60.4 mmol) in water (20 mL) over 30 minutes at 0° C. To the mixture was added dropwise a solution of $SnCl_2 \cdot 2H_2O$ (37.2 g, 165 mmol) in concentrated HCl (45 mL) over 1 hour. After stirring for 2 hours at 0° C., the reaction mixture was basified with 50% NaOH (50 mL). The mixture was further diluted with water (50 mL) and treated with another 50% NaOH (20 mL) and then crushed ice (200 g). The reaction mixture was extracted with ether (3×200 mL) and the combined organic phases were washed with brine, dried over $Na_2SO_4$, and filtered. The filtrate was acidified by adding an anhydrous solution of HCl in ether (2 N in ether, 42 mL, 82.5 mmol). The precipitate was collected and dried under reduced pressure to give 9.92 g (71%) of title compound as a pale yellow solid. $^1$H NMR (DMSO): 300 MHz δ 10.18 (bs, 3H), 7.98 (bs, 1H), 7.21 (m, 2H), 2.16 (s, 3H).

4-Bromo-5-fluoro-7-methyl Tryptophol

To a solution of 5-bromo-4-fluoro-2-methylphenylhydrazine hydrochloride (4.75 g, 18.6 mmol) in 20% aqueous THF (100 mL) at 0° C. was added dropwise a solution of 2,3-dihydrofuran (1.55 mL, 20.4 mmol) in THF (10 mL). After stirring for 2 hours at 0° C. and 12 hours at room temperature, the reaction mixture was diluted with ether (100 mL).

The organic solution was washed with saturated $NaHCO_3$ (2×100 mL) and brine (100 mL), dried ($Na_2SO_4$) and concentrated. The residue was dissolved in ethylene glycol (50 mL), treated with $ZnCl_2$ (5.58 g, 40.9 mmol), and heated at 170° C. for 4 hours. The reaction mixture was cooled down to room temperature and 6 N HCl (100 mL) was added. The mixture was extracted with ether (3×100 mL) and washed with water (200 mL) and brine (200 mL). The organic solution was dried over $Na_2SO_4$ and concentrated. The residue was purified by flash chromatography (silica, 40% EtOAc in hexanes) to give 1.52 g (30%) of title compound containing inseparable impurities (<20%) as a light brown oil. $^1$H NMR (CDCl3): 300 MHz δ 8.68 (bs, 1H), 7.06 (d, J=2.4 Hz, 1H), 6.76 (d, J=9.63 Hz, 1H), 3.92 (t, J=6.48 Hz, 2H), 3.21 (t, J=6.48 Hz, 2H), 2.35 (s, 3H), 2.27 (bs, 1H).

5-Bromo-6-fluoro-8-methyl-1-propyl-1,3,4,9-tetrahydropyrano[3,4-b]indole-1-acetic Acid Ethyl Ester To a solution of 4-bromo-7-methyl tryptophol (400 mg g, 1.47 mmol) and ethyl butyrylacetate (0.28 mL, 1.76 mmol) in $CH_2Cl_2$ (5 mL) was added $BF_3 \cdot OEt_2$ (0.22 mL, 1.76 mmol) dropwise at room temperature. The solution was stirred for 2 hours and then washed with saturated aqueous $NaHCO_3$ (5 mL) and brine (5 mL). The organic phase was dried ($Na_2SO_4$) and concentrated. The residue was purified by flash chromatography (silica, 15% EtOAc in hexanes) to give 496 mg (82%) of title compound as a pale yellow solid. Mp=137–138° C.; $^1$H NMR (CDCl$_3$): 300 MHz δ 9.73 (bs, 1H), 6.76 (d, J=10.1 Hz, 1H), 4.21 (m, 2H), 4.05 (m, 1H), 3.91 (m, 1H), 3.05–2.89 (m, 4H), 2.53 (s, 3H), 2.07 (m, 1H), 1.92 (m, 1H), 1.38 (m, 1H), 1.30 (t, J=6.98 Hz, 3H), 1.21 (m, 1H), 0.89 (t, J=7.08 Hz, 3H).

5-Cyano-6-fluoro-8-methyl-1-propyl-1,3,4,9-tetrahydropyrano[3,4-b]indole-1-acetic Acid Ethyl Ester -Bromo-6-fluoro-8-methyl-1-propyl-1,3,4,9-tetrahydropyrano[3,4-b]indole-1-acetic acid ethyl ester (496 mg, 1.20 mmol) and CuCN (162 mg, 1.81 mmol) was dissolved in N-methyl-2-pyrrolidinone (6 mL) and the solution was divided into the 2 microwave reaction vessels (3.0 mL each). The reaction vessels were heated in microwave at 220° C. for 15 minutes. The reaction mixtures in 2 vessels were combined and then diluted with water (10 mL). The crude mixture was extracted with EtOAc (3×20 mL). The combined organic phase was washed with brine (50 mL), dried over $Na_2SO_4$ and concentrated. The residue was purified by flash chromatography (silica, 25% EtOAc in hexanes) to give 404 mg (94%) of title compound as a white solid. $^1$H NMR (DMSO): 300 MHz δ 12.02 (bs, 1H), 11.33 (bs, 1H), 7.00 (d, J=9.00 Hz, 1H), 3.96 (m, 2H), 2.95 (d, J=10.3 Hz, 1H), 2.83 (t, J=3.9 Hz, 1H), 2.72 (d, J=10.3 Hz, 1H), 2.54 (s, 3H), 1.99 (m, 2H), 1.28 (m, 1H), 0.85 (m, 1H), 0.79 (t, J=5.41 Hz, 3H).

5-Cyano-6-fluoro-8-methyl-1-propyl-1,3,4,9-tetrahydropyrano[3,4-b]indole-1-acetic Acid To a solution of 5-cyano-6-fluoro-8-methyl-1-propyl-1,3,4,9-tetrahydropyrano[3,4-b]indole-1-acetic acid ethyl ester (404 mg, 1.13 mmol) in THF/MeOH (2.5 mL/5 mL) was added 1 N NaOH (2.26 mL, 2.26 mmol). The reaction mixture was stirred at ambient temperature overnight. Most of THF/MeOH was removed under reduced pressure and the resulting mixture was acidified with 1 N HCl. The mixture was extracted with EtOAc (3×10 mL). The combined organic phase was washed with brine (20 mL), dried over $Na_2SO_4$ and concentrated to provide 341 mg (91%) of title compound as a white solid. $^1$H NMR (DMSO): 300 MHz δ 12.02 (bs, 1H), 11.33 (bs, 1H), 7.00 (d, J=9.00 Hz, 1H), 3.96 (m, 2H), 2.95 (d, J=10.3 Hz, 1H), 2.83 (t, J=3.9 Hz, 1H), 2.72 (d, J=10.3 Hz, 1H), 2.54 (s, 3H), 1.99 (m, 2H), 1.28 (m, 1H), 0.85 (m, 1H), 0.79 (t, J=5.41 Hz, 3H).

[(R)-5-cyano-6-fluoro-8-methyl-1-propyl-1,3,4,9-tetrahydropyrano[3,4-b]indol-1-yl]acetic acid Preparative HPLC using CHIRALPACK-AD (250×20 mm) and 10% isopropyl alcohol in heptane (0.1% TFA) as eluant gave (R) and (S) enantiomers of 5-cyano-6-fluoro-8-methyl-1-propyl-1,3,4,9-tetrahydropyrano[3,4-b]indole-1-acetic acid as white solids. HRMS (ESI) [M+H]$^+$ calculated for $C_{18}H_{20}FN_2O_3$ 331.1453, found 331.1447 (R enantiomer) and 331.1452 (S enantiomer); Chiral HPLC HP 1100 with spiderlink CHIRALPACK-AD, 250×4.6 mm, isopropyl alcohol/heptane containing 0.1% TFA (10:90), 1.0 mL/minutes, DAD 215 nm; $t_R$=7.19 minutes (R enantiomer), 9.27 minutes (S enantiomer).

Alternatively, [(R)-5-cyano-8-methyl-1-propyl-1,3,4,9-tetrahydropyrano[3,4-b]indol-1-yl]acetic acid can be obtained by resolution with cinchonine according to the procedure described for example 1.

What is claimed is:

1. A pharmaceutical composition comprising a compound of a formula:

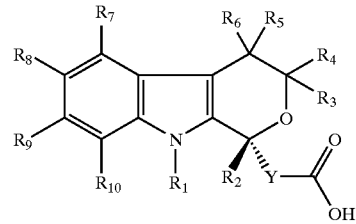

wherein:
R$_1$ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;

R$_2$ is n-propyl, sec-butyl or cyclobutyl;

R$_3$–R$_4$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or $R_5$ and $R_6$ together with the ring carbon atom to which they are attached form a carbonyl group;

$R_5$–$R_6$ are H;

$R_7$ is halo or CN;

$R_8$–$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, alkylthio of 1 to 8 carbon atoms, trifluoromethoxy, trifluoroethoxy, trifluoromethylthio, trifluoroethylthio, acyl of 1 to 6 carbon atoms, COOH, COO-alkyl, $CONR_{11}R_{12}$, F, Cl, Br, I, CN, $CF_3$, $NO_2$, alkylsulfinyl of 1 to 8 carbon atoms, alkylsulfonyl of 1 to 6 carbon atoms, pyrrolidinyl, or thiazolidinyl;

$R_{11}$–$R_{12}$ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl;

Y is $CH_2$; or a crystalline form or a pharmaceutically acceptable salt thereof; and a pharmaceutically acceptable carrier.

2. The pharmaceutical composition of claim 1 comprising a compound of the formula:

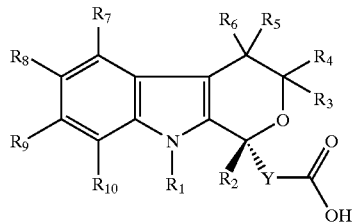

wherein:

$R_1$ is H, a straight chain alkyl of 1 to 6 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, or an arylalkyl of 7 to 12 carbon atoms;

$R_3$–$R_4$ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, furanylmethyl, an arylalkyl of 7 to 12 carbon atoms, an alkynyl of 2 to 7 carbon atoms, or $R_5$ and $R_6$ together with the ring carbon atom to which they are attached form a carbonyl group;

$R_8$–$R_{10}$ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, an unsubstituted heteroaryl or a heteroaryl substituted with one to three groups, furanylmethyl, an arylalkyl of 7 to 12 carbon atoms, an alkynyl of 2 to 7 carbon atoms, phenylalkynyl, an alkoxy of 1 to 6 carbon atoms, an arylalkoxy of 7 to 12 carbon atoms, an alkylthio of 1 to 6 carbon atoms, trifluoromethoxy, trifluoroethoxy, trifluoromethylthio, trifluoroethylthio, an acyl of 1 to 6 carbon atoms, a carboxy group, $CONR_{11}R_{12}$, F, Cl, Br, I, CN, $CF_3$, $NO_2$, an alkylsulfinyl of 1 to 6 carbon atoms, an alkylsulfonyl of 1 to 6 carbon atoms;

$R_{11}$–$R_{12}$ are independently H, a straight chain alkyl of 1 to 6 carbon atoms, a branched alkyl of 3 to 10 carbon atoms, a cycloalkyl of 3 to 10 carbon atoms, an aryl substituted with one to four groups, an unsubstituted heteroaryl or a heteroaryl substituted with one to three groups; or a crystalline form or a pharmaceutically acceptable salt thereof.

3. A compound of a formula;

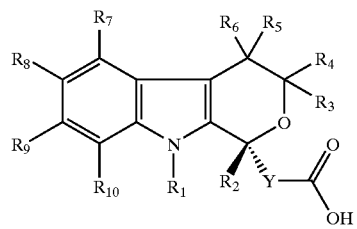

wherein:

$R_1$ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl of 7 to 12 carbon atoms;

$R_2$ is n-propyl, sec-butyl or cyclobutyl;

$R_3$–$R_4$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms;

$R_5$–$R_6$ are H;

$R_7$ is halo or CN;

$R_8$–$R_{10}$ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, an unsubstituted heteroaryl or a heteroaryl substituted with one to three groups, furanylmethyl, an arylalkyl of 7 to 12 carbon atoms, an alkynyl of 2 to 7 carbon atoms, phenylalkynyl, an alkoxy of 1 to 6 carbon atoms, an arylalkoxy of 7 to 12 carbon atoms, an alkylthio of 1 to 6 carbon atoms, trifluoromethoxy, trifluoroethoxy, trifluoromethylthio, trifluoroethylthio, an acyl of 1 to 6 carbon atoms, a carboxy group, $CONR_{11}R_{12}$, F, Cl, Br, I, CN, $CF_3$, $NO_2$, an alkylsulfinyl of 1 to 6 carbon atoms, an alkylsulfonyl of 1 to 6 carbon atoms;

$R_{11}$–$R_{12}$ are independently H, a straight chain alkyl of 1 to 6 carbon atoms, a branched alkyl of 3 to 10 carbon atoms, a cycloalkyl of 3 to 10 carbon atoms, an aryl substituted with one to four groups, an unsubstituted heteroaryl substituted with one to three groups;

Y is $CH_2$; or a crystalline form or a pharmaceutically acceptable salt thereof.

4. The compound of claim 3 wherein;

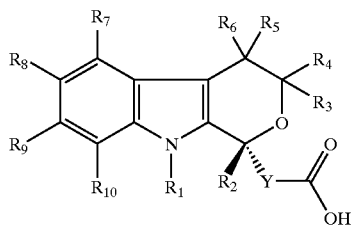

R₁ is H, a straight chain alkyl of 1 to 6 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, or an arylalkyl of 7 to 12 carbon atoms;

R₃–R₄ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, furanylmethyl, an arylalkyl of 7 to 12 carbon atoms, an alkynyl of 2 to 7 carbon atoms, or R₅ and R₆ together with the ring carbon atom to which they are attached form a carbonyl group; or a crystalline form or a pharmaceutically acceptable salt thereof.

5. A compound selected from the group consisting of:
[(R)-5-cyano-8-methyl-1-propyl-1,3,4,9-tetrahydropyrano[3,4-b]indol-1-yl]acetic acid;
[(R)-5-cyano-8-fluoro-1-propyl-1,3,4,9-tetrahydropyrano[3,4-b]indol-1-yl]acetic acid;
[(R)-5,8-dichloro-1-propyl-1,3,4,9-tetrahydropyrano[3,4-b]indol-1-yl]acetic acid; and
[(R)-5-cyano-6-fluoro-8-methyl-1-propyl-1,3,4,9-tetrahydropyrano[3,4-b]indol-1-yl]acetic acid; or a crystalline form or a pharmaceutically acceptable salt thereof.

6. The compound of claim 3 wherein:

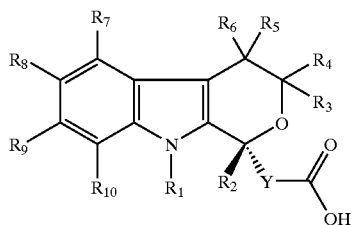

R₁ is H;
R₂ is n-propyl;
R₃–R₆ are H;
R₇ is Cl or CN;
R₈–R₁₀ are independently H, straight chain alkyl of 1 to 3 carbon, F, Cl, or CN;
Y is CH₂; or
crystalline form; or a pharmaceutically acceptable salt thereof.

7. The pharmaceutical composition of claim 1 wherein the compound is present in an enantiomerically pure form.

8. A pharmaceutical composition comprising a compound having a ratio of isomer A to isomer B of at least about 7:1 and is defined by the formulas:

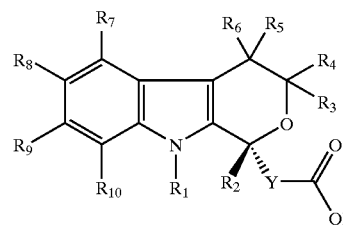

Isomer (A)

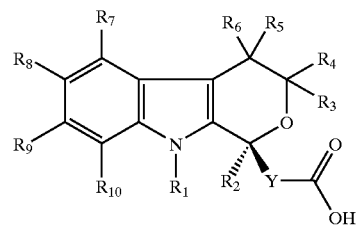

and isomer (B)

wherein:
R₁ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;
R₂ is n-propyl, sec-butyl or cyclobutyl;
R₃–R₄ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or R₅ and R₆ together with the ring carbon atom to which they are attached form a carbonyl group;
R₅–R₆ are H;
R₇ is halo or CN;
R₈–R₁₀ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, alkylthio of 1 to 8 carbon atoms, trifluoromethoxy, trifluoroethoxy, trifluoromethylthio, trifluoroethylthio, acyl of 1 to 6 carbon atoms, COOH, COO-alkyl, CONR₁₁R₁₂, F, Cl, Br, I, CN, CF₃, NO₂, alkylsulfinyl of 1 to 8 carbon atoms, alkylsulfonyl of 1 to 6 carbon atoms, pyrrolidinyl, or thiazolidinyl;
R₁₁–R₁₂ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl;
Y is CH₂; or
a crystalline form or a pharmaceutically acceptable salt thereof; and
a pharmaceutically acceptable carrier.

9. The pharmaceutical composition of claim 8, wherein the ratio of isomer A to isomer B is at least about 8:1.

10. The pharmaceutical composition of claim 9, wherein the ratio of isomer A to isomer B is at least about 9:1.

11. The pharmaceutical composition of claim 1 wherein the compound in the composition is selected from the group consisting of:

[(R)-5-cyano-8-methyl-1-propyl-1,3,4,9-tetrahydropyrano[3,4-b]indol-1-yl]acetic acid;

[(R)-5-cyano-8-fluoro-1-propyl-1,3,4,9-tetrahydropyrano[3,4-b]indol-1-yl]acetic acid;

[(R)-5,8-dichloro-1-propyl-1,3,4,9-tetrahydropyrano[3,4-b]indol-1-yl]acetic acid; and

[(R)-5-cyano-6-fluoro-8-methyl-1-propyl-1,3,4,9-tetrahydropyrano [3,4-b]indol-1-yl]acetic acid.

12. The pharmaceutical composition of claim 1 wherein:

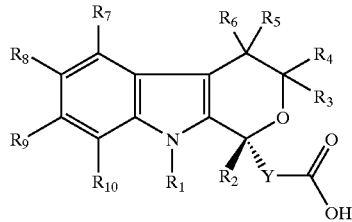

$R_1$ is H;
$R_2$ is n-propyl;
$R_3$–$R_6$ are H;
$R_7$ is Cl or CN;
$R_8$–$R_{10}$ are independently H, a straight chain alkyl of 1 to 3 carbon, F, Cl, or CN; or
a crystalline form or a pharmaceutically acceptable salt thereof.

13. A method of obtaining the isomer of a compound of claim 3 comprising:

a. dissolving a racemic mixture of a compound of claim 3 in 2-butanone with a chiral amine;

b. heating to obtain a solution;

c. stirring and cooling the solution of step (b) to obtain a first solid and a liquid;

d. isolating, the solid of step (c) from the liquid of step (c);

e. washing with 2-butanone and drying the solid from step (d);

f. repeating step (c) on the liquid of step (d) to obtain a second solid;

g. combining the first and second solids and treating the combined solids with HCl and ethyl acetate to obtain an ethyl acetate layer and a liquid layer;

h. washing the ethyl acetate layer of step (g) with 1N HCl and water to obtain a liquid layer;

i. combining the liquid layers from step (g) and step (h);

j. extracting the combined layers from step (i) with ethyl acetate;

k. washing the ethyl acetate layer from step (j) with water;

l. drying, filtering and concentrating the ethyl acetate layer to obtain a solid;

m. triturating the solid of step (l) with ethyl acetate to obtain a precipitate and a liquid;

n. drying the precipitate obtained in step (h) to obtain a compound of claim 3; and o. repeating steps (l) and (m) on the liquid of step (m) to obtain additional compound of claim 3.

14. The method of claim 13 wherein the chiral amine is an ephedrine hemihydrate or cinchomine.

* * * * *